United States Patent
Heimbecher et al.

(10) Patent No.: US 9,023,790 B2
(45) Date of Patent: May 5, 2015

(54) POSACONAZOLE INTRAVENOUS SOLUTION FORMULATIONS STABILIZED BY SUBSTITUTED β-CYCLODEXTRIN

(75) Inventors: Susan K. Heimbecher, Morris Plains, NJ (US); David Monteith, Pittstown, NJ (US); James D. Pipkin, Lawrence, KS (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 10 days.

(21) Appl. No.: 13/704,145

(22) PCT Filed: Jun. 24, 2011

(86) PCT No.: PCT/US2011/041715
§ 371 (c)(1),
(2), (4) Date: Dec. 13, 2012

(87) PCT Pub. No.: WO2012/005973
PCT Pub. Date: Jan. 12, 2012

(65) Prior Publication Data
US 2013/0096053 A1 Apr. 18, 2013

Related U.S. Application Data

(60) Provisional application No. 61/359,701, filed on Jun. 29, 2010.

(51) Int. Cl.
*A61K 9/00* (2006.01)
*A61K 31/496* (2006.01)
*A61K 31/724* (2006.01)

(52) U.S. Cl.
CPC ............. *A61K 9/0019* (2013.01); *A61K 31/496* (2013.01); *A61K 31/724* (2013.01)

(58) Field of Classification Search
None
See application file for complete search history.

(56) References Cited

U.S. PATENT DOCUMENTS

| | | | |
|---|---|---|---|
| 7,629,331 B2 | 12/2009 | Pipkin et al. | |
| 8,410,077 B2 | 4/2013 | Antle | |
| 2003/0099674 A1 | 5/2003 | Chen | |
| 2006/0009469 A1* | 1/2006 | Witchey-Lakshmanan et al. | 514/254.07 |
| 2006/0116411 A1* | 6/2006 | Yada et al. | 514/383 |
| 2008/0097372 A1 | 4/2008 | Shimizu et al. | |
| 2009/0270348 A1* | 10/2009 | Antle | 514/58 |

FOREIGN PATENT DOCUMENTS

WO 2007-047253 A2 4/2007

OTHER PUBLICATIONS

Tran et al. Int'l J Pharma Compounding. 10(3);202-204:2006.*
PubChem. NCBI. Posaconazole. Retreived Nov. 26, 2013.*
PubChem. NCBI. Captisol. Retreived Nov. 26, 2013.*
Nomeir, A.A., et al., "Pharmacokinetics of SCH 56592, a New Azole Broad-Spectrum Antifungal Agent, in Mice, Rats, Rabbits, Dogs, and Cynomolgus Monkeys", Antimicrobial Agents and Chemotherapy, 2000, pp. 727-731, vol. 44, No. 3.
Groll, A.H., et al., Antifungal Efficacy and Pharmacodynamics of Posaconazole in Experimental Models of Invasive Fungal Infections, Mycoses, 2006, pp. 7-16, vol. 49, Suppl. 1.
Frampton, J.E., et al., "Posaconazole: A Review of Its Use in the Prophylaxis of Invasive Fungal Infections", Drugs, 2008, pp. 993-1016, vol. 68, No. 7.
Captisol® + FAQ + Solution and Solid State Characteristics in Captisol®. Captisol a Ligand Company, 11119 North Torrey Pines Rd., LaJolla, CA 92037, n.d. Web. Mar. 6, 2014. <http://www.captisol.com/faq/solution-and-solid-state-characteristics-in-captisol/>. (2 pages).
Captisol® + FAQ + Cyclodextrins General. Captisol a Ligand Company, 11119 North Torrey Pines Rd., LaJolla, CA 92037, n.d. Web. Mar. 6, 2014. <http://www.captisol.com/faq/cyclodextrins-general//>. (2 pages).
PCT International Preliminary Report on Patentability—PCT/US11/041715, Jan. 8, 2013.
PCT International Search Report—PCT/US11/041715, Oct. 28, 2011.
Sistla, A., et al, "Developement of an Intravenous Formulation of SU010382 (Prodrug Of SU5416, An Anti-Angiogenesis Agent," PDA Journal of Pharmaceutical Science and Technology, May 2008, pp. 200-210, vol. 62, No. 3.
Tinwalla, A.Y., et al, "Solubization of Thiazolobenzimidazole Using a Combination of Ph Adjustment and Complexation With 2-Hydroxypropyl-Beta-Cyclodextrin", Pharmaceutical Research, Spring, New York, LLC, Aug. 1, 1993, pp. 1136-1143, vol. 10, No. 8.
"Sporanox", Drugs.com, Jun. 2006, pp. 1-17.

* cited by examiner

*Primary Examiner* — Amber D Steele
*Assistant Examiner* — Schuyler Milton
(74) *Attorney, Agent, or Firm* — Carol S. Quagliato; Laura M. Ginkel (57) ABSTRACT

The present invention relates to aqueous solutions useful as pharmaceutical compositions of posaconazole for intravenous administration. These compositions include a solubilizing agent, such as a modified β-cyclodextrin in an acidified solution, which can also include a chelating agent such as disodium edetate (EDTA). In clinical trials, a 200 mg posaconazole dose of the selected composition was found to achieve acceptable pharmacokinetic properties.

19 Claims, 8 Drawing Sheets

POSACONAZOLE INTRAVENOUS SOLUTION FORMULATIONS STABILIZED BY SUBSTITUTED β-CYCLODEXTRIN

FIELD OF THE INVENTION

The present invention relates to aqueous pharmaceutical compositions of posaconazole and a complexing agent. Such pharmaceutical compositions provide sufficient solubilization of posaconazole to result in improved shelf life of the product and reduced likelihood of precipitation during injection into a vein or an intravenous drip tube.

The invention also relates to methods for treating and/or preventing fungal infections using said pharmaceutical compositions.

BACKGROUND OF THE INVENTION

U.S. Pat. Nos. 5,703,079 and 5,661,151 (see Column 69, ex. 24) disclose posaconazole, a broad spectrum anti-fungal agent, the structure of which is illustrated below:

U.S. Pat. No. 6,958,337 discloses crystalline forms of posaconazole. United States Patent Application 20060160823 describes a formulation consisting of an injectable suspension. A solid (capsule/tablet) of posaconazole is disclosed in U.S. Pat. Nos. 5,972,381 and 5,834,472.

Posaconazole is marketed as an oral suspension (40 mg/ml) under the trademark NOXAFIL™ in the United States by Merck (formerly Schering Corporation, Kenilworth, N.J.). NOXAFIL™ (posaconazole) is indicated for prophylaxis of invasive *Aspergillus* and *Candida* infections in patients, 13 years of age and older, who are at high risk of developing these infections due to being severely immunocompromised, such as hematopoietic stem cell transplant (HSCT) recipients with graft-versus-host disease (GVHD) or those with hematologic malignancies with prolonged neutropenia from chemotherapy. NOXAFIL™ (posaconazole) is also indicated for the treatment of oropharyngeal candidiasis, including oropharyngeal candidiasis refractory to itraconazole and/or fluconazole.

Posaconazole is a weakly basic and poorly-aqueous soluble drug that has poor bioavailability and variable absorption. Posaconazole has a solubility of less than 1 µg/mL in neutral and basic aqueous solutions. Although the solubility increases under acidic conditions (e.g., 3 µg/mL at pH 3 and 0.8 mg/mL at pH 1), a more dramatic increase in solubility would be required to meet the projected daily intravenous dosage of more than 100 mg.

Thus, it would be advantageous to have available to patients an intravenous solution formulation to boost the bioavailability of posaconazole. An injectable formulation would also allow administration to patients that cannot be given oral dosage forms, such as in the case of patients who have difficulty swallowing or who are unconscious. Of course, any such intravenous formulation would have to display chemical and physical stability over the shelf life of the product.

SUMMARY OF THE INVENTION

In some embodiments, the invention is directed to a pharmaceutical composition for intravenous administration comprising:
  posaconazole, or a pharmaceutically acceptable salt thereof; and,
  a modified β-cyclodextrin,
  in aqueous solution, wherein the pH of said composition is between about 2.0 and about 3.5.

In further embodiments, said modified β-cyclodextrin comprises sulfobutylether-β-cyclodextrin.

In further embodiments, the composition further comprises a chelating agent.

In further embodiments, said pharmaceutical composition comprises posaconazole free base, said modified β-cyclodextrin comprises sulfobutylether-cyclodextrin, said chelating agent comprises EDTA, and wherein said pH is between about 2.3 and about 3.0.

In further embodiments, posaconazole free base concentration is between about 14 and about 22 mg/ml, sulfobutylether-β-cyclodextrin concentration is between about 350 and about 450 mg/mL, and EDTA concentration is between about 0.1 and about 0.3 mg/mL.

In further embodiments, posaconazole free base concentration is about 18 mg/mL, sulfobutylether-β-cyclodextrin concentration is about 400 mg/mL, and EDTA concentration is about 0.2 mg/mL.

In further embodiments, an administration of a dose of said composition that delivers 200 mg of posaconazole to a patient results in a $C_{max}$ of between about 1176 and about 18375 ng/ml, and an $AUC_{last}$ of between about 21,600 and about 33,750 hr*ng/ml.

In further embodiments, an administration of a dose of said composition that delivers 200 mg of posaconazole to a patient results in a $C_{max}$ of about 1470 ng/ml and an $AUC_{last}$ of about 27,000 hr*ng/ml.

In further embodiments, said pharmaceutical composition for intravenous administration comprises components and the quantities of each as follows:

| Components | Quantity |
| --- | --- |
| Posaconazole | about 5 to about 25 mg/mL |
| Captisol ® (sulfobutylether-β-cyclodextrin) | about 25 mM to about 200 mM |
| Disodium Edetate (EDTA) | about 0.1 to about 1.0 mg/mL |
| 1N Hydrochloric Acid | quantity sufficient to adjust to pH of about 2.0 to about 3.0 |
| 1N Sodium Hydroxide | quantity sufficient to adjust to pH of about 2.0 to about 3.0 |
| Water | q.s. ad 1 mL |

In further embodiments, said pharmaceutical composition comprises components and the quantities of each as follows:

| Components | Quantity |
| --- | --- |
| Posaconazole | about 18 mg/mL |
| Captisol ® (sulfobutylether-β-cyclodextrin) | about 400 mg/mL (185 mM) |
| Disodium Edetate (EDTA) | about 0.2 mg/mL |
| 1N Hydrochloric Acid | quantity sufficient to adjust to pH of about 2.6 |
| 1N Sodium Hydroxide | quantity sufficient to adjust to pH of about 2.6 |
| Water | q.s. ad 1 mL |

In further embodiments, the invention is directed to a method of treating or preventing an infection in an animal in need thereof which comprises administering to said animal an effective amount of any of the pharmaceutical compositions above.

In further embodiments, infection is caused by a fungus or a parasite.

In further embodiments, infection is one or more selected from the group consisting of: oropharyngeal or esophageal candidiasis; refractory oropharyngeal and esophageal candidiasis; invasive aspergillosis, candidiasis, fusarriosis, scedosporiosis, infections due to dimorphic fungi, zygomycosis, and invasive infections due to rare molds and yeasts; invasive mycoses in patients who are refractory to, or intolerant of, other therapies; Candidiasis, invasive mold infections in patients who have undergone intensive chemotherapy and/or radiation therapy for hematologic malignancies, bone marrow or peripheral stem cell transplant conditioning regimes, and patients receiving combination immunosuppressive therapy for the treatment of acute or chronic graft-versus-host disease or prevention of solid organ transplantation; Chagas disease; and Leishmaniasis.

In further embodiments, after said composition has been injected into an infusion bag, the composition and the infusate have been admixed, and the resulting admixture has been allowed to stand for up to 24 hours, no posaconazole precipitate is visible.

In further embodiments, the method comprises administering to said animal the composition of claim 1 in an amount sufficient to deliver a dose of between about 180 and about 220 mg posaconazole to said animal.

In further embodiments, the method comprises administering to said animal the composition of claim 1 in an amount sufficient to deliver a dose of about 200 mg posaconazole to said animal.

In further embodiments, an administration occurs once per day.

In further embodiments, an administration occurs twice per day.

In further embodiments, the method further comprises administering a second active ingredient selected from one or more of the group consisting of antifungals, antibacterials, antivirals, steroids, nonsteroidal anti-inflammatory drugs, chemotherapeutics and anti-emetics.

In further embodiments, antifungals are selected from the group consisting of azoles, echinocandin, allylamine, polyene, flucytosine, benzoic acid, ciclopirox, 1,3-dihydro-5-fluoro-1-hydroxy-2,1-benzoxaborate, tolnaftate, undecyclenic acid, griseofulvin and haloprogin.

In further embodiments, the invention is directed to a kit comprising:
  a small, breakable container;
  an infusion bag;
  and the composition,
  wherein said container contains the composition,
  and said infusion bag contains a diluent selected from the group consisting of normal saline solution and 5% dextrose solution,
and wherein said small, breakable container is placed directly inside said infusion bag suitably to allow said composition to be diluted by breaking said small, breakable container directly inside diluent in said infusion bag.

DETAILED DESCRIPTION OF THE INVENTION

Various approaches were taken in the pursuit of a stable solution of posaconazole that would be useful as an intravenous formulation of sufficient bioavailability and other pharmaceutically desired characteristics.

Posaconazole Intravenous Solutions

Cyclodextrins, and their derivatives, are known to display the characteristic of enhancing the aqueous solubility of certain compounds, as taught in U.S. Pat. No. 5,134,127. However, this reference is silent as to whether or not cyclodextrins can enhance the aqueous solubility of posaconazole, or any related azole compounds. Example 32 of U.S. Pat. No. 7,635, 773 purports to teach the stabilization of posaconazole with sulfobutyl ether-β-cyclodextrin ($SBE_{66}$-β-CD) that had undergone single or double treatment with activated carbon.

Captisol® is the trade name for a sulfobutyl ether-β-cyclodextrin shown below, and marketed by CyDex Pharmaceuticals, Inc., Lenexa, Kans. The chemical structure of Captisol® is as follows:

Table 1 displays certain relevant information regarding Captisol®.

TABLE 1

| Names | Sulfobutyl ether-β-cyclodextrins, (SBE-β-CD) sodium salt |
|---|---|
| Molecular weight | 2163 g/mole (Degree of substitution = 6.5) |
| Solubility | >800 mg/mL in water |
| CAS no. | 182410-00-0 |

This compound is used as a complexing agent to improve the solubility and/or stability of pharmaceutical compounds.

In an effort to evaluate the range of posaconazole solubilities that could be achieved at feasible pH's, a series of solutions was prepared with a fixed Captisol® concentration. Utilizing an acidic solution of 20% Captisol® (w/v), the solubility of posaconazole was increased more than 1000 times and it was determined that a target concentration of 5 mg/mL could be achieved. Table 2 displays posaconazole solubilities in 20% Captisol® solutions at various pH values.

TABLE 2

| pH | Posaconazole Solubility (mg/mL) |
|---|---|
| 3.0 | 8.7 |
| 3.1 | 7.8* |
| 3.2 | 6.9 |
| 3.4 | 5.2 |
| 3.6 | 4.0 |
| 3.8 | 3.1 |

*Calculated - average of the measured solubility at pH 3.0 and pH 3.2.

Figure 1:
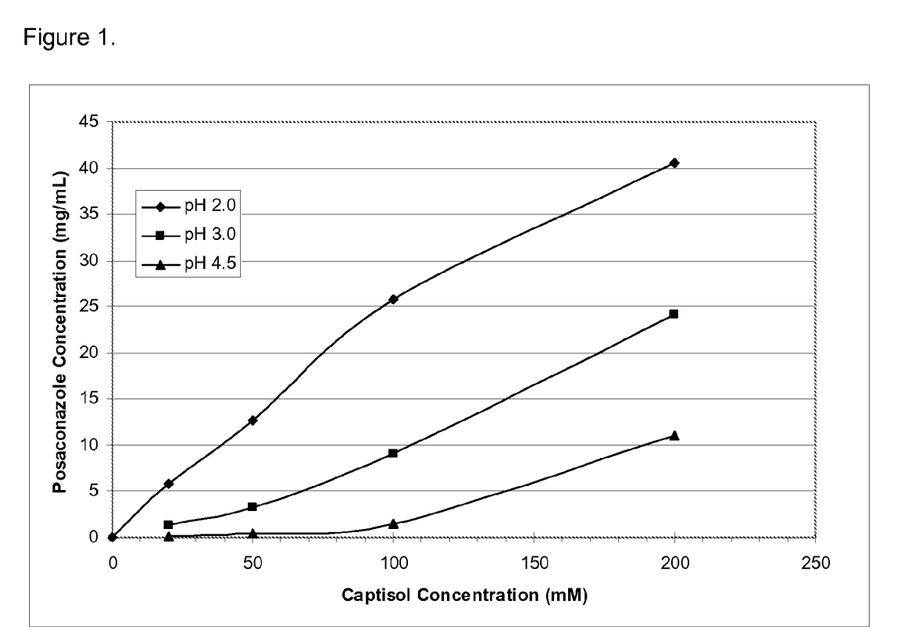
FIG. 1 displays the solubility of posaconazole versus Captisol® concentration at different pH values.

Posaconazole solubility was also evaluated in acidified solutions with different Captisol® concentrations. As shown in FIG. 1, posaconazole solubility increases with pH, as well as Captisol® concentration. However, FIG. 1 also shows that at each pH the increase in posaconazole solubility is non-linear with respect to the Captisol®, and at pH 3.0 and 4.5, there is a greater than linear increase in posaconzole concentration. Therefore, at some pH values, as the Captisol® concentration increases, the ratio of Captisol® to solubilized posaconazole will decrease. Based on this solubility effect, a formulation could be developed whereby for the same posaconazole daily dosage, the daily dose of Captisol® could be decreased. For example at a pH of 3.1, the posaconazole solubility in 20% Captisol® was calculated to be 7.8 mg/mL (see Table 2), whereas in 40% Captisol®, the solubility was determined to be 22.5 mg/mL. In this case the Captisol® concentration was increased by a factor of 2 whereas, the posaconazole solubility was increased by a factor of 2.9.

However, if increasing Captisol® concentration has a greater than linear effect on posaconazole solubility, the opposite effect would also be expected, i.e., dilution of Captisol® solutions containing posaconazole at or near posaconazole equilibrium solubility should result in precipitation of posaconazole. This effect is of significance in that the preferred delivery of the posaconazole formulation is dilution with either normal saline or 5% dextrose, followed by infusion. Surprisingly however, following dilution of the posaconazole/Captisol® formulation, no precipitation was seen for at least 24 hours.

Hydrochloric acid was used as an acidifier in the posaconazole formulation. However, several additional acidifiers (i.e., citric, sulfuric, maleic, phosphoric, acetic, L-tartaric, D-tartaric, DL-tartaric, methanesulfonic, naphthalenesulfonic, p-toluenesulfonic, lactic, L-lactic, L-ascorbic and malic acid, as well as, glycine hydrochloride) were also evaluated in regard to posaconzole solubilization. However, at the same pH, no improvement in solubility was seen with these acidifiers.

In an effort to explore further improvements to the formulation, the effects of various co-solvents and non-ionic surfactants, on the solubility of posaconazole in a 100 mM Captisol® solution, were examined. The Captisol® solutions were adjusted with HCl to pH 4.5 and an appropriate amount of co-solvent was added. An excess amount of posaconazole was added to the pH-adjusted cyclodextrin/co-solvent solution and the solutions were allowed to equilibrate for a period of three days. The contents of the vials were then centrifuged and the supernatant was assayed for posaconazole.

Table 3 shows the impact of the various co-solvents and several surfactants (0.1% 0.2% v/v Poloxamer F-68, Tween 20 or Tween 80) on the solubility of posaconazole. The surfactants that were tested did not enhance the solubility of posaconazole, and the co-solvents decreased the solubility.

TABLE 3

| Co-solvent | Posaconazole (mg/mL) |
|---|---|
| Control (100 mM Captisol ®) | 1.77 |
| 10% Propylene Glycol | 0.41 |
| 10% PEG 400 | 1.28 |
| 10% PVP | 0.64 |
| 0.1% Poloxamer F-68 | 1.63 |
| 0.1% Tween 20 | 1.71 |
| 0.1% Tween 80 | 1.74 |

Figure 2:
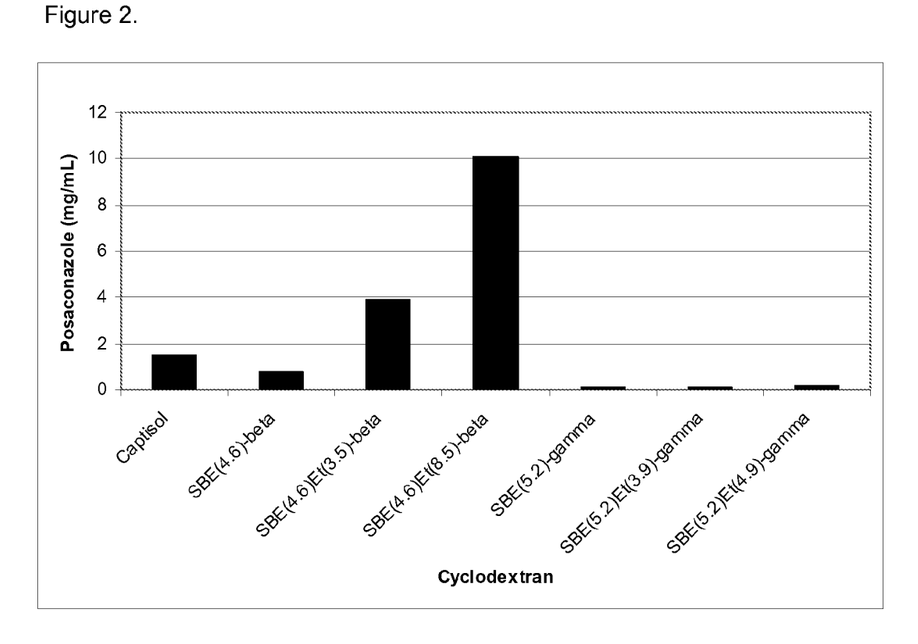
FIG. 2 is a histogram displaying the solubility of posaconazole with various sulfobutyl ether-β-cyclodextrins (SBE-CyDs) at 100 mM and pH 4.5.

The solubilities of posaconazole in each of several modified β and γ-cyclodextrins were evaluated. Solubilization of posaconazole was tested with three gamma cyclodextrins; SBE (5.2)-gamma, SBE (5.2) Et (3.9)-gamma and SBE (5.2) Et (4.9)-gamma cyclodextrin, (CyDex, Inc.). At cyclodextrin concentrations of 100 mM and pH 4.5, the highest posaconazole solubility achieved was 0.189 mg/mL, approximately 8 fold less than the 1.51 mg/mL achieved with Captisole, SBE (6.5) –β cyclodextrin, under similar conditions (See FIG. 2).

On the other hand, some changes in β-cyclodextrin substitutions did lead to greater solubilization. Utilizing 100 mM cyclodextrin solutions at pH 4.5, solubilization of posaconazole with SBE (4.6) –β, SBE (4.6) –Et (3.5) –β and SBE (4.6) –Et (8.5) –β cyclodextrins, versus Captisol®, was evaluated. The SBE (4.6) –Et (3.5) –β and SBE (4.6) –Et (8.5) –β cyclodextrins solubilized 2.6 and 6.6 fold more posaconazole (respectively) than did Captisol® (See FIG. 2). However, the extensive Captisol® safety information outweighed the potential benefits of greater solubilization and, for this reason, formulations with other sulfobutyl ether cyclodextrins were not further developed.

Finally, stability screening studies also showed that Captisol® formulations of posaconazole undergo color changes under accelerated conditions. Solutions of 10 mg/mL posaconazole, in 40% Captisol® at pH 3.0, were prepared, both with and without 1 mg/mL EDTA, and with and without nitrogen overlay. After 20 days at 40° C., the solutions were evaluated for color changes with a colorimeter, whereby color formation is indicated by a "b*" value (solutions with a b* value of 3 or greater appear yellow). As shown in Table 4, the development of color was minimized by both EDTA and nitrogen overlay. However, in the solution containing EDTA, no additional improvement was seen by inclusion of a nitrogen overlay.

TABLE 4

| Description | EDTA level | $N_2$ | b* |
|---|---|---|---|
| 10 mg/mL Posaconazole, 200 mM Captisol ® | 0.0 mg/mL | No | 4.17 |
| 10 mg/mL Posaconazole, 200 mM Captisol ® | 1.0 mg/mL | No | 1.49 |
| 10 mg/mL Posaconazole, 200 mM Captisol ® | 0.0 mg/mL | Yes | 2.33 |
| 10 mg/mL Posaconazole, 200 mM Captisol ® | 1.0 mg/mL | Yes | 1.67 |

Stability condition: 40° C./75% RH for 20 days

Based on these studies, as well as further formulation screening, EDTA is used in the current formulation at level of 0.2 mg/mL, which is suitable for parenteral delivery. In addition, although posaconazole is stable in acidified Captisol® solutions under room temperature and accelerated conditions, as described below, a storage temperature of 5° C. is suggested in order to further minimize development of yellow color.

Figure 3:
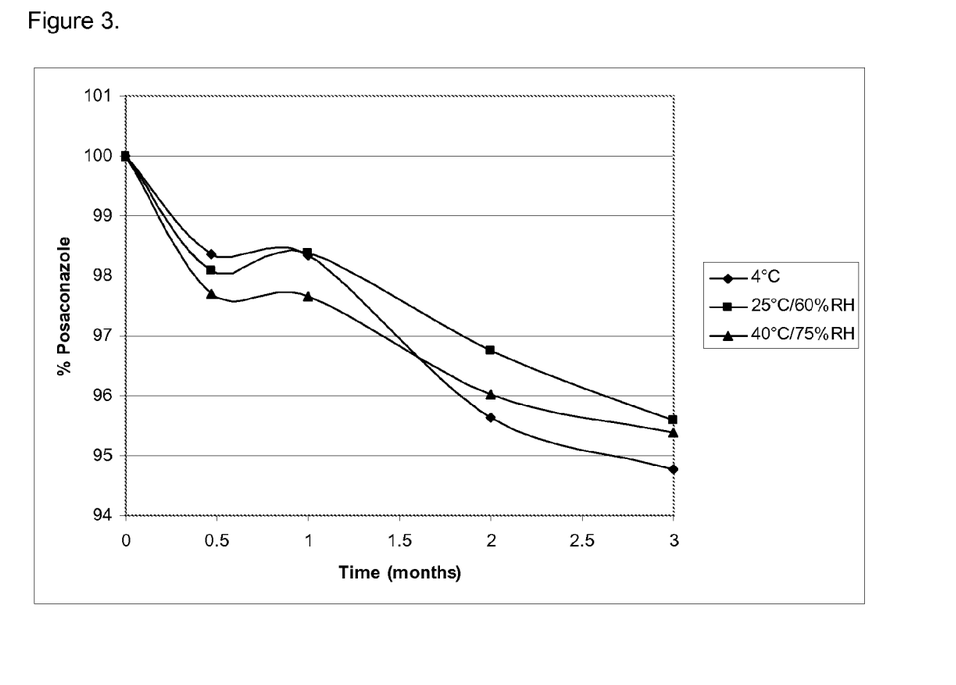
FIG. 3 displays the percentage posaconazole (10 mg/mL) remaining in solution over time in 200 mM Captisol® solution at pH 3.0.

A set of studies was conducted to explore the stability of posaconazole solutions of varied composition and pH. The accelerated stability of 10 mg/mL posaconazole in a 200 mM Captisol® solution at pH 3.0 was examined over a period of three months. Posaconazole was added to a pH-adjusted solution of 200 mM Captisol® and mixed for 24 hours. The solution was then filtered and placed on stability at 4° C., 25° C./60% RH, and 40° C./75% RH. The sample did not contain a chelating agent and was not sparged with nitrogen. Results are shown in FIG. 3. The temperature had minimal impact on the degradation of posaconazole over the three month time period. However, the solution became pale yellow within two weeks and grew darker with time. Thus, it was concluded that the chelating agent is important to obtain compositions according to the present invention.

Figure 4:
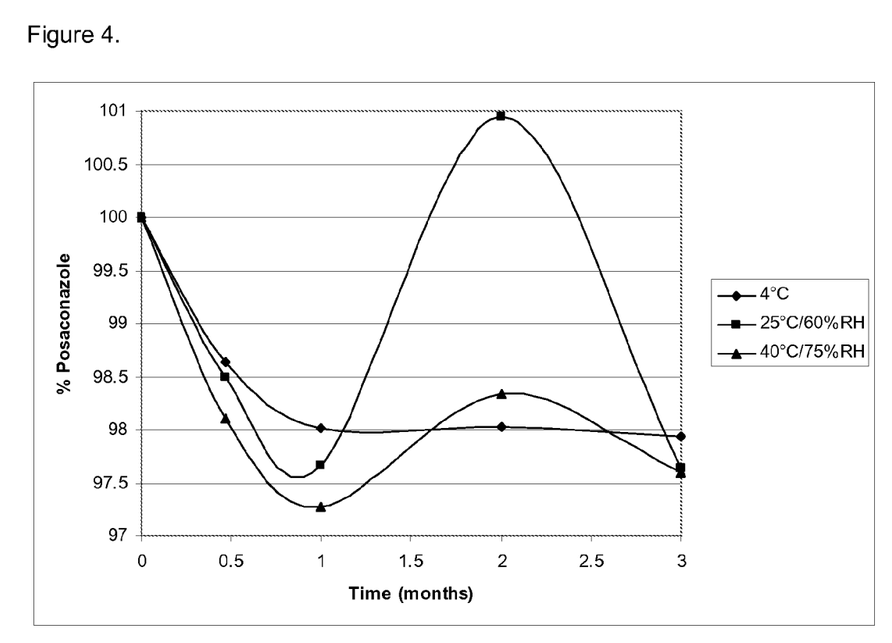
FIG. 4 displays the percentage posaconazole (5 mg/mL) remaining in solution over time in 100 mM Captisol® solution at pH 3.0.

A similar time study of the stability of posaconazole (5 mg/mL) in 100 mM Captisol® solution at pH 3.0 was conducted over a period of three months. Posaconazole was added to a pH-adjusted solution of 100 mM Captisol® and mixed for 24 hours. The solution was then filtered and placed on stability at 4° C., 25° C./60% RH, and 40° C./75% RH. The sample did not contain a chelating agent and was not sparged with nitrogen. Results are shown in FIG. 4. The temperature had minimal impact on the degradation of posaconazole over the three month time period. However, the solution became pale yellow within two weeks and grew darker with time.

A study of the stability of posaconazole (18 mg/mL) in 400 mg/mL Captisol® solution at pH 3.0 was also conducted over a period of nine months. The sample was manufactured using the most current clinical manufacturing process. EDTA was dissolved in water for injection. Captisol® was then dissolved in the EDTA solution and the solution was then acidified with HCl. Posaconazole was then added and dissolved. Additional HCl was added to the solution, as necessary to adjust the pH. The solution was also sparged with nitrogen during the entire process.

Figure 5:
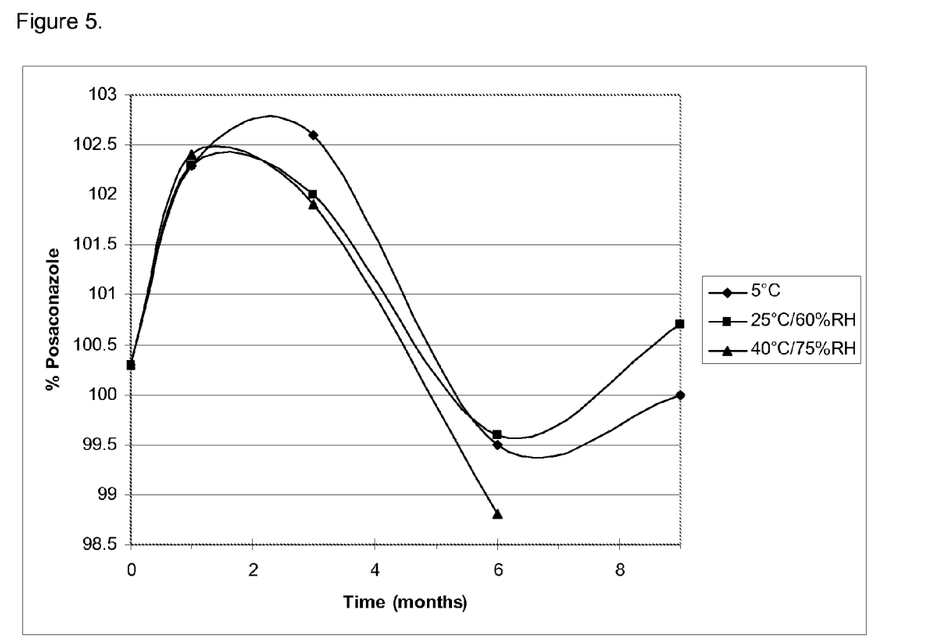
FIG. 5 displays the percentage posaconazole (18 mg/mL) remaining in solution over time in 400 mg/mL Captisol® solution at pH 2.6.

The prepared solution was then aseptically filtered, filled into vials, and placed on stability under different storage conditions. As shown in FIG. 5, the temperature had minimal impact on the degradation of posaconazole over the nine month time period.

Several prototype formulations, based on either solutol HS 15 (Macrogol® 15 hydroxysterate Ph. Eur.) or cyclodextrins, were also evaluated. These formulations were found to have sufficient physical and chemical stability to support further development but, as described below, toxicological testing showed unexpectedly superior results for the 40% Captisol® formulation.

Six prototype formulations, reflected in Tables 5 and 6, were prepared.

Table 5 displays the composition of three Solutol® based formulations (nos. 1-3) and Table 6 displays the compositions of another three cyclodextrin based formulations (nos. 4-6).

These six formulations were the subject of a toxicological screening study using the suspension formula as a control. The formulations were dosed to rats via intravenous infusion for 15 min. over a period of 2 weeks. The posaconazole dose for all animals was 10 mg/Kg. In addition, the hemolytic potential of each formula was tested in vitro prior to dosing.

TABLE 5

Posaconazole IV Solutions: Solutol Based

| Ingredients | No. 1: 30% Solutol (as is - no dilution) mg/mL | No. 2: 30% Solutol (1:5 dilution with NS[1]) mg/mL | No. 3: 75% Solutol (1:5 dilution with NS) mg/mL |
|---|---|---|---|
| posaconazole | 10 | 10 | 10 |
| Solutol HS 15 | 300 | 300 | 750 |
| Ethanol | 240 | 240 | 150 |
| Polyethylene glycol 200 | 220 | 220 | — |
| Lactic acid | 50 | 50 | — |
| 0.9% Saline q.s. ad | — | — | 1 mL |
| Water for Injection q.s. ad | 1 mL | 1 mL | — |

[1]Normal Saline

TABLE 6

Posaconazole IV Solutions: Cyclodextrin Based

| Ingredients | No. 4: 30% HPβCD[1] (1:5 dilution with D5W[2]) mg/mL | No. 5: 20% Captisol ® (1:2.5 dilution with D5W) mg/mL | No. 6: 40% Captisol ® (1:10 dilution with NS[3]) mg/mL |
|---|---|---|---|
| posaconazole | 10 | 5 | 20 |
| Captisol ® | — | 200 | 400 |
| HPβCD | 200 | — | — |
| EDTA | — | — | 0.1 |
| Tartaric Acid | 9 | — | — |
| Hydrochloric Acid | — | to pH 3 | to pH 3 |
| Sodium Hydroxide | to pH 3.5 | — | — |
| Water for Injection q.s. ad | 1 mL | 1 mL | 1 mL |

[1]Hydroxypropyl-beta-cyclodextrin
[2]5% Dextrose
[3]Normal Saline

One prototype (Formula No. 1), was directly infused. However, the remaining formulas were all diluted to a concentration of 2 mg posaconazole 1 mL before infusion.

The results of the toxicity screening study are summarized below.

The 30% solutol formulation that was directly injected (Formula No. 1) produced hemolysis in the in vitro screening and showed severe local intolerance. and in vivo hemolysis was indicated. This study was stopped before completion and the animals were sacrificed.

The 30% solutol formulation that was diluted 1:5 before infusion (Formula No. 2) produced hemolysis in vitro, similar to that produced by Formula No. 1. Based on this result, animals were not dosed.

The 75% solutol formulation that was diluted 1:5 before infusion (Formula No. 3) showed some evidence of hemolysis in vitro (time dependent). In addition, clinical signs of local intolerance were seen in some animals.

Similar results were seen for both the 20% HPβCD formulation, diluted 1:5 before infusion (Formula No. 4), and the 20% Captisol® formulation, diluted 1:2.5 before infusion (Formula No. 5). For both formulations, the in vitro hemolysis testing showed no hemolysis but, slight effects on rat kidney tubule cells were seen. In addition, animal studies have suggested that HPβCD sterile dosage forms have significant toxicological potential.

The 40% Captisol® formulation (Formula No. 6) was diluted 1:10 before infusion. This formulation did not produce hemolysis in vitro and showed no clinical signs of toxicity or effects on clinical pathology parameters.

Thus, only the 40% Captisol® formulation had no toxicological findings and, interestingly, this formulation was also superior to the 20% Captisol® formulation. The reason for this difference is assumed to be that, for an equivalent posaconazole dose, the 20% formulation requires twice as much Captisol® as that of the 40% formulation.

The final formulation, based on the 40% Captisol® solution, included modifications to ensure posaconazole solubilization over any potential variability in the formulation. For example, both a target pH and an acceptable pH range are required for manufacturing, and the formulation must be stable over the entire specified range. In order to meet these criteria, the concentration of posaconazole was reduced slightly, from 20 mg/mL to 18 mg/mL, and the pH was reduced from 3.0 to 2.6.

The clinical composition of intravenous posaconazole solution formulation is shown in Table 7.

TABLE 7

| Components | Quantity | Range |
|---|---|---|
| Posaconazole | 18 mg/mL | 5 to 25 mg/mL |
| Captisol ® (sulfobutylether-β-cyclodextrin) | 400 mg/mL (185 mM) | 25 mM to 200 mM |
| Disodium Edetate (EDTA) | 0.2 mg/mL | 0.1 to 1.0 mg/mL |
| 1N Hydrochloric Acid | pH adjust (pH 2.6) | pH 2.0 to 3.0 |
| 1N Sodium Hydroxide | pH adjust (pH 2.6) | pH 2.0 to 3.0 |
| Water | q.s. ad 1 mL | q.s. ad 1 mL |

Several formulation dilution studies were conducted as described below.

A dilution study was conducted in order to evaluate the likelihood of precipitation during dilution prior to administration to a patient. A ten percent excess of the required amount posaconazole was weighed into an amber vial. Captisol® solution adjusted to the target pH using HCl was added to the vial. The vial was capped and gently mixed at room temperature for 24 hours. After 24 hours, the test vials were filtered through 0.22 micron Millipore PVDF Millex-GV® filter. A portion of the filtered sample (10 mL) was added to a 100 mL volumetric flask. The sample was diluted to the 100 mL mark with either 0.9% Sodium Chloride Injection USP (normal saline) or 5% Dextrose Injection USP ("D5W"). Samples were observed for 24 hours at 4° C. and ambient temperature.

The results of using normal saline and D5W as diluents are summarized in Tables 8 and 9. Solid precipitate was visually observed in the following formulations of posaconazole 24 hours after dilution with normal saline: 20 mg/mL posaconazole in 200 mM Captisol® at pH 3, 3 mg/mL posaconazole in 100 mM Captisol® at pH 4, and 5 mg/mL posaconazole in 150 mM or 200 mM Captisol® at pH 4. All of the other diluted samples were clear after 24 hours. Solid precipitate was visually observed in the following formulations of posaconazole 24 hours after dilution with D5W: 5 mg/mL posaconazole at pH 3, 10 mg/mL posaconazole at pH 3, 20 mg/mL posaconazole in 200 mM Captisol® at pH 3, 3 mg/mL posaconazole in 100 or 200 mM Captisol® at pH 4, and 5 mg/mL posaconazole in 150 mM Captisol® at pH 4. All of the other diluted samples were clear after 24 hours. This experiment indicates that it is possible to prepare posaconazole formulations that will not precipitate out when diluted for delivery to the patient.

TABLE 8

| | Dilution Study in Normal Saline | | | | | |
|---|---|---|---|---|---|---|
| | Initial | | 4° C. (24 hours) | | Ambient (24 hours) | |
| Sample | Apperance | % Posaconazole[a] | Apperance | % Posaconazole[a] | Apperance | % Posaconazole[a] |
| Posaconazole 20 mg/mL 100 mM Captisol ® at pH 2 | Clear Solution | 100.00 | Clear solution | 102.52 | Clear solution | 102.59 |

TABLE 8-continued

Dilution Study in Normal Saline

| Sample | Initial | | 4° C. (24 hours) | | Ambient (24 hours) | |
|---|---|---|---|---|---|---|
| | Apperance | % Posaconazole[a] | Apperance | % Posaconazole[a] | Apperance | % Posaconazole[a] |
| Posaconazole 20 mg/mL 200 mM Captisol ® at pH 2 | Clear Solution | 100.00 | Clear solution | 102.37 | Clear solution | 99.99 |
| Posaconazole 5 mg/mL 100 mM Captisol ® at pH 3 | Clear Solution | 100.00 | Clear solution | 100.29 | Clear solution | 100.26 |
| Posaconazole 10 mg/mL 200 mM Captisol ® at pH 3 | Clear Solution | 100.00 | Clear solution | 103.18 | Clear solution | 102.1 |
| Posaconazole 20 mg/mL 200 mM Captisol ® at pH 3 | Clear Solution | 100.00 | Solid | 102.75 | Solid | 101.20 |
| Posaconazole 3 mg/mL 100 mM Captisol ® at pH 4 | Clear Solution | 100.00 | Solid | 101.56 | Solid | 99.33 |
| Posaconazole 3 mg/mL 200 mM Captisol ® at pH 4 | Clear Solution | 100.00 | Clear solution | 100.93 | Clear solution | 100.27 |
| Posaconazole 5 mg/mL 150 mM Captisol ® at pH 4 | Clear Solution | 100.00 | Solid | 101.22 | Solid | 99.94 |
| Posaconazole 5 mg/mL 200 mM Captisol ® at pH 4 | Clear Solution | 100.00 | Solid | 101.30 | Solid | 99.59 |

[a]Versus initial value after dilution.

TABLE 9

Dilution Study in D5W

| Sample | Initial | | 4° C. (24 hours) | | Ambient (24 hours) | |
|---|---|---|---|---|---|---|
| | Apperance | % Posaconazole[a] | Apperance | % Posaconazole[a] | Apperance | % Posaconazole[a] |
| Posaconazole 20 mg/mL 100 mM Captisol ® at pH 2 | Clear Solution | 100.00 | Clear solution | 99.35 | Clear solution | 100.19 |
| Posaconazole 20 mg/mL 200 mM Captisol ® at pH 2 | Clear Solution | 100.00 | Clear solution | 99.01 | Clear solution | 97.21 |
| Posaconazole 5 mg/mL 100 mM Captisol ® at pH 3 | Clear Solution | 100.00 | Solid | 100.99 | Solid | 100.05 |
| Posaconazole 10 mg/mL 200 mM Captisol ® at pH 3 | Clear Solution | 100.00 | Solid | 99.90 | Solid | 99.05 |
| Posaconazole 20 mg/mL 200 mM Captisol ® at pH 3 | Clear Solution | 100.00 | Solid | 100.39 | Solid | 101.05 |
| Posaconazole 3 mg/mL 100 mM Captisol ® at pH 4 | Clear Solution | 100.00 | Solid | 100.72 | Solid | 99.72 |
| Posaconazole 3 mg/mL 200 mM Captisol ® at pH 4 | Clear Solution | 100.00 | Solid | 101.12 | Solid | 100.69 |
| Posaconazole 5 mg/mL 150 mM Captisol ® at pH 4 | Clear Solution | 100.00 | Solid | 101.13 | Solid | 100.01 |
| Posaconazole 5 mg/mL 200 mM Captisol ® at pH 4 | Clear Solution | 100.00 | Clear Solution | 101.63 | Clear Solution | 102.53 |

[a]Versus initial value after dilution.

In order to further evaluate the potential for precipitation during infusion of the diluted solution into a vein, a dynamic precipitation study was performed by using a Yalkowsky et al. method (J. L. H. Johnson, Y. He, S. H. Yalkowsky, Validation of an In Vitro Model for Prediction of In Vivo Phlebitis, *AAPS*, 2002, poster #14919) with small modifications. The flow rate of isotonic Sorenson's phosphate buffer (ISPB) was 5 mL/min which is comparable to that of human blood flow in readily accessible veins.

A peristaltic pump (Master Flex® model 7518-10) provided flow of an aqueous phase at a rate of 5 mL/min through flexible tubing (Cole-Parmer's L/S 14 Silicone (Platinum) which has an internal diameter of 1.6 mm), then through a UV flow-cell. The aqueous phase served as a blood surrogate and consisted of isotonic Sorenson's phosphate buffer (ISPB) at pH 7.4. The sample solution was injected into the tubing through a needle inserted 30 cm upstream of the flow cell. A syringe pump was used to control the rate of sample injection. The injection rate varied from 0.05 to 10 mL/min. The appearance of a precipitate was detected by Beckman DU-7 spectrophotometer at 540 nm. This study was conducted at room temperature. The filtered test sample was diluted 1:10 with normal saline or D5W before injection.

Results of the dynamic precipitation study for samples injected at 1.0 mL/min are illustrated in Table 10. The results of dynamic precipitation study suggest that various formulations can be prepared and diluted without resulting in precipitation. Less precipitation was also seen in samples injected at rates less than 1.0 mL/min.

TABLE 10

| | pH 2 | pH 3 | pH 4 |
|---|---|---|---|
| | 200 mM Captisol ® | | |
| Posaconazole 20 mg/mL | Precipitation[a] | Cannot prepare | Cannot Prepare |
| Posaconazole 10 mg/mL | Clear[b] | Clear[b] | Cannot Prepare |

TABLE 10-continued

|  | pH 2 | pH 3 | pH 4 |
|---|---|---|---|
| Posaconazole 5 mg/mL | Clear[b] | Clear[b] | Clear[b] |
| Posaconazole 3 mg/mL | Clear[b] | Clear[b] | Clear[b] |
| 150 mM Captisol ® | | | |
| Posaconazole 20 mg/mL | Precipitation[a] | Cannot prepare | Cannot prepare |
| Posaconazole 10 mg/mL | Not Tested | Not Tested | Cannot prepare |
| Posaconazole 5 mg/mL | Clear[b] | Clear[b] | Cannot prepare |
| Posaconazole 3 mg/mL | Clear[b] | Clear[b] | Clear[b] |
| 100 mM Captisol ® | | | |
| Posaconazole 20 mg/mL | Precipitation[a] | Cannot prepare | Cannot prepare |
| Posaconazole 10 mg/mL | Precipitation[a] | Cannot prepare | Cannot prepare |
| Posaconazole 8 mg/mL | Clear[b] | Clear[b] | Cannot prepare |
| Posaconazole 5 mg/mL | Clear[b] | Clear[b] | Cannot prepare |
| Posaconazole 3 mg/mL | Clear[b] | Clear[b] | Cannot prepare |

[a]Precipitation after in-vitro dynamic injection
[b]No precipitation after in-vitro dynamic injection Methods of Manufacture The clinical posaconazole intravenous formulation can be prepared according to the following methods:

Posaconazole can be prepared according to methods described in Examples 24 and 32 of U.S. Pat. No. 5,661,151 and WO95/17407.

The intravenous solution concentrate can be prepared according to the following procedure:

Charge an initial volume of water for injection (WFI) into vessel.

Add EDTA to WFI in vessel and mix until dissolved.

Add SBE-β-cyclodextrin to WFI in vessel and mix until dissolved.

Filter an appropriate volume of EDTA+SBE-β-cyclodextrin solution through a clarifying filter into the main compounding vessel. The total filtered volume of EDTA+SBE-β-cyclodextrin solution is dependent on the mixing efficiencies of the equipment used during compounding.

Add 1N HCl to vessel in order to acidify the filtered solution.

Add posaconazole into the filtered solution. When compounding with equipment that provides sufficient agitation, posaconazole may be charged as a powder. When compounding with equipment that provides limited agitation pre-wet the posaconazole in WFI in a separate vessel using a ratio of one part posaconazole to five parts water (1:5 ratio) and mix until a homogeneous suspension is formed.

Add pre-wetted posaconazole suspension to main vessel and mix until dissolved.

Add any additional 1N HCl or 1N NaOH in order to adjust the pH to the appropriate level.

q.s. ad water for injection to obtain the final batch volume and mix to obtain a homogenous solution.

Aseptic filter pharmaceutical composition through a 0.22 μm filter. Package filtered product into 6RDIN glass vials. Stopper and crimp cap.

The solution is sparged with nitrogen during the compounding process.

During the development of the manufacturing method, different manufacturing procedures were evaluated including optimizing the Posaconazole: WFI ratio, changing the order of excipient addition, and charging the powder excipients concurrently. Based on the development studies, the above detailed manufacturing method provides the optimal manufacturing process for the solution.

Commercial-Scale Manufacturing

Figure 6:
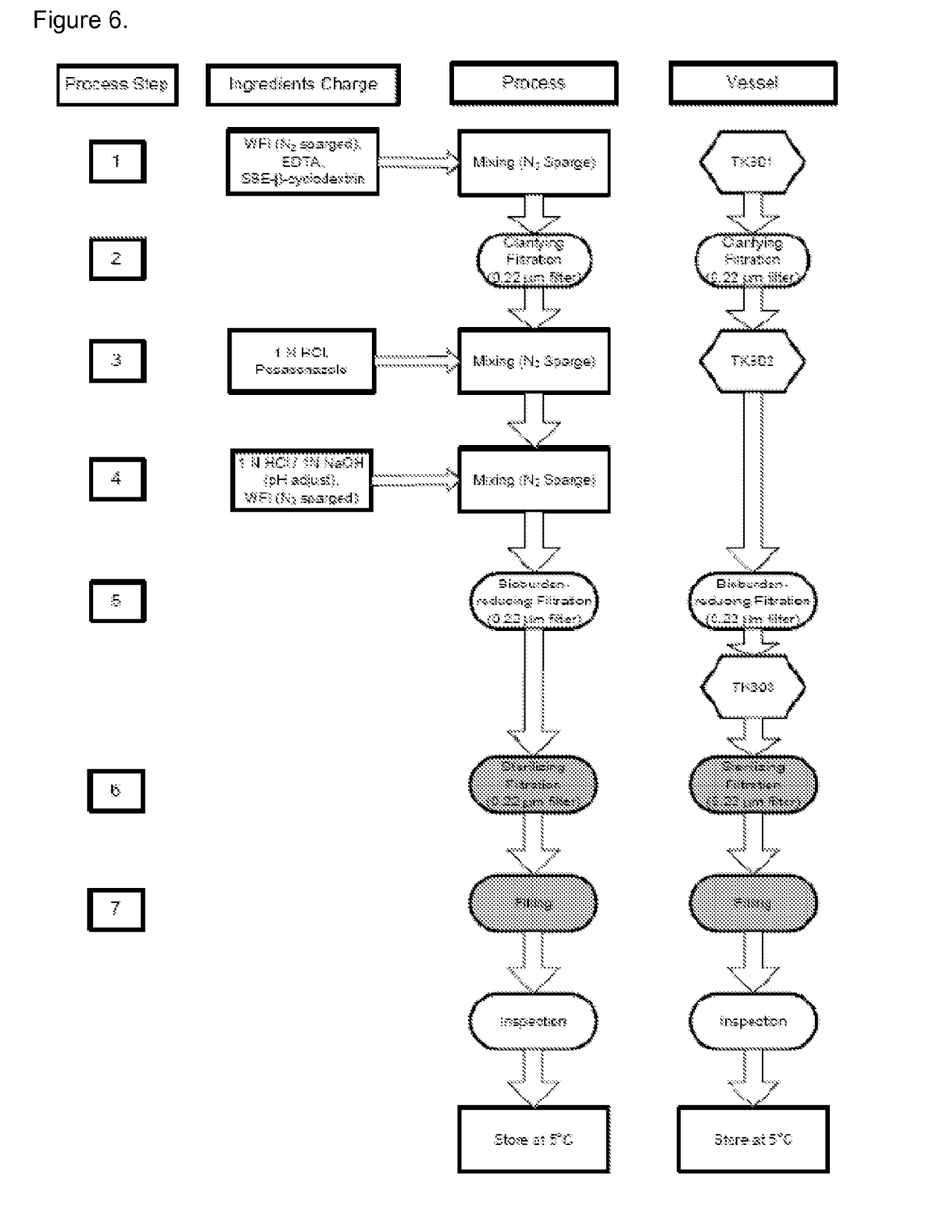
FIG. 6 displays the process flow diagram for the commercial scale developmental batches.

A three vessel manufacturing process was used for the 200 L commercial-scale batches. To ensure adequate mixing, overhead mixers were utilized to help dissolve the captisol and posaconazole. Nitrogen sparging was utilized during the compounding process. FIG. 6 displays the process flow diagram for the commercial scale developmental batches, which process is summarized as follows:

The EDTA and captisol are dissolved in nitrogen-sparged Water for Injection (WFI) in the first vessel. The EDTA+captisol solution is then filtered through a 0.22 μm clarifying membrane filter into the drug product compounding vessel.

In the drug product compounding vessel, the filtered EDTA+captisol solution is acidified with hydrochloric acid, and the API is charged into the acidified solution. The solution is mixed until the API dissolves. The pH is then adjusted to 2.6 using hydrochloric acid and/or sodium hydroxide as necessary, and the product is brought to final volume.

The drug product is then filtered through a 0.22 μm bioburden reducing membrane filter into a receiving vessel. From the receiving vessel, the solution is sterilized through an in-line 0.22 μm sterilizing filter and aseptically filled and stoppered into sterile, depyrogenated glass vials in a Grade A filling area.

Diluted IV Infusion (Admixture)

The diluted intravenous solution (admixture) for infusion can be prepared according to the following procedure:

The following concentrations and dose ranges bracket the lower and upper levels of the rising single dose study defined in the clinical protocol.

Low dose, 150 mg (1 mg/mL admixture):

Allow the posaconazole Injectable solution, 18 mg/mL drug product to equilibrate to room temperature. Gently invert the drug product vial ten times.

Remove an appropriate volume of diluent (0.9% NaCl or 5% dextrose) from admixture bag so that 142 mL of diluent remains in the bag.

Withdraw 8.4 mL of posaconazole injectable solution, 18 mg/mL with an appropriately sized syringe and inject the entire amount of drug product into the IV bag. Mix the contents of the bag with ten gentle inversions.

High dose, 450 mg (3 mg/mL admixture):

Allow the posaconazole Injectable solution, 18 mg/mL drug product to equilibrate to room temperature. Gently invert the drug product vial ten times.

Remove an appropriate volume of diluent (0.9% NaCl or 5% dextrose) from admixture bag so that 125 mL of diluent remains in the bag.

Withdraw 25 mL of posaconazole injectable solution, 18 mg/mL with an appropriately sized syringe and inject the entire amount of drug product into the IV bag. Mix the contents of the bag with ten gentle inversions.

Trial in Healthy Subjects

A Phase 1, single-site, randomized, evaluator-blind (within dose level) placebo-controlled, single-dose study was conducted to evaluate the pharmacokinetics, safety and tolerability of posaconazole intravenous solution when administered as single dose and as multiple doses. The first group, received a single dose of posaconazole 200 mg. Posaconazole intravenous was admixed in 150 mL of 5% dextrose to provide a final concentration of approximately 1.33 mg/mL of posaconazole in solution for the 200 mg dose, and was infused in a peripheral vein in the arm over 90 minutes. Although central line administration is generally recommended to infuse low pH formulations, the lack of signal in nonclinical toxicology studies supported the use of posaconazole intravenous solution administered via peripheral lines in this study.

A cohort of 12 subjects (9 active and 3 dextrose placebo) received a single infusion of posaconazole intravenous solution on Day 1. Six out of 9 subjects experienced post-infusion local reactions, manifested as erythema, induration and tenderness. One subject had extravasation and resulting arm swelling. The events were reported between 4 and 24 hours post-infusate. Local intolerability is likely due to the irritation caused by the low pH of the infusate, administered slowly via peripheral lines. The local intolerability observed prompted the discontinuation of this trial in healthy volunteers that received posaconazole intravenous via peripheral infusion. Alternative infusion strategies (rapid or slow infusion via peripheral lines) will be explored in healthy volunteers. Formulations with low pH are better tolerated if infused via central lines. Therefore, a strategy was designed to continue the program in patients with central lines.

Figure 7:
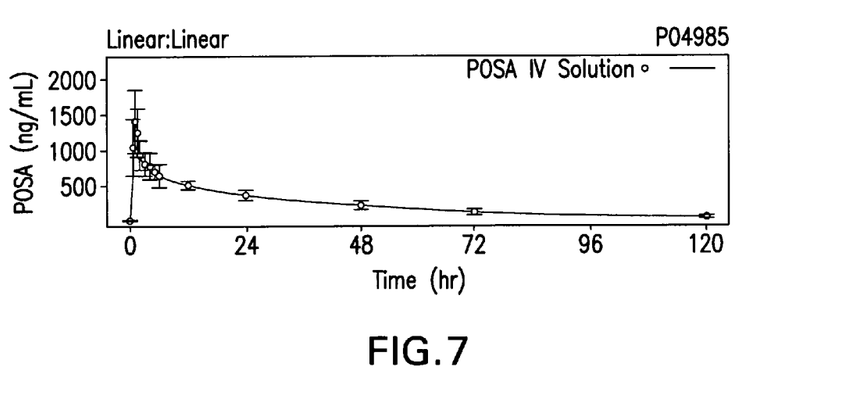
FIG. 7 displays mean (±80) posaconazole plasma concentration-time profiles following single dose, intravenously administered, 200 mg posaconazole intravenous solution of posaconazole to healthy adult volunteers.

The pharmacokinetic profile of posaconazole intravenous was typical of an intravenous drug (see FIG. 7) with low variability. Median $T_{max}$ was 1 hour, mean $C_{max}$ 1470 ng/mL, mean AUC(0-24) 13,500 hr·ng/mL, (estimated $C_{avg}$ 563 ng/mL) and variability for all parameters around 25% or less.

Table 11 displays Mean (CV %) posaconazole Plasma Pharmacokinetic Parameters of Posaconazole Following Single Dose, 200 mg Intravenous Solution of Posaconazole to Healthy Adult Volunteers (All Subjects Included).

TABLE 11

| Treatment | Day | $C_{max}$ (ng/mL) | $T_{max}{}^a$ (hr) | $AUC_{tf}$ (hr*ng/mL) | AUC(I) (hr*ng/mL) | $t_{1/2}$ (hr) | Vd/F (L) | $C_{avg}{}^b$ (ng/mL) |
|---|---|---|---|---|---|---|---|---|
| POS IV Solution (200 mg; Treatment A: n = 9) | 1 | 1470 (24) | 1.00 (1.00-4.00) | 27000 (23) | 28100 (26) | 24.3 (22) | 254 (17) | 1170 (26) (Range: 904-1900) |

IV = intravenous,
$C_{max}$ = maximum observed plasma concentration;
$T_{max}$ = time to $C_{max}$;
$AUC_{tf}$ = Area under the curve from time zero to last quantifiable sample;
AUC(I) = area under the plasma concentration-time curve from time 0-infinity;
$t_{1/2}$ = terminal phase half-life,
Vd/F = Apparent volume of distribution;
$C_{avg}$ = Projected average concentration at steady state . . .
$^a$Median (minimum, maximum).
$^b$Values for $C_{avg}$ are projected with no adjustments for possible time dependencies.

$C_{max}$ and $T_{max}$ were observed pharmacokinetic parameters. Individual plasma concentration data were used to estimate the following pharmacokinetics parameters: AUC(tf), AUC (I), $t_{1/2}$, Vd/F, and $C_{avg}$. The terminal phase rate constant (k) was calculated as the negative of the slope of the log-linear terminal portion of the plasma concentration-time curve using linear regression. The $t_{1/2}$ was calculated as: $t_{1/2}=\ln(2)/K$. The AUC(tf) was calculated using the linear trapezoidal method and extrapolated to infinity, AUC(I), as follows: AUC (I)=AUC(tf)/Cest$_{tf}$/k, where Cest$_{tf}$ is the estimated concentration at the time of the last measurable sample, determined from the linear regression of the terminal portion.

As shown in Table 11, the $C_{avg}$ range following 200 mg single dose is anticipated to be about 900 to about 1900 ng/mL that meets the target $C_{avg}$ targeted for bridging with posaconazole oral suspension. Therefore, the likely dose is 200 mg QD, provided patient pharmacokinetic data are no different than the healthy volunteer data and no non-linearity is observed upon the multiple dosing.

Figure 8:
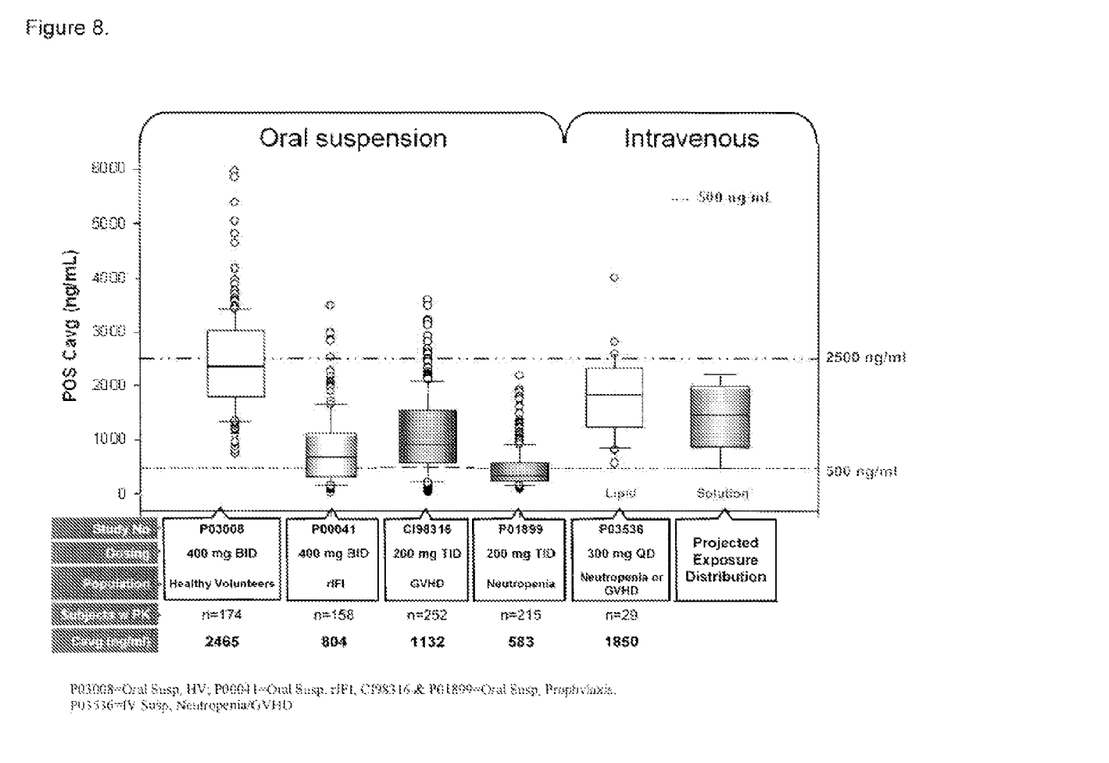
FIG. 8 displays a summary of observed posaconazole steady-state exposures and the projected exposure distribution for the posaconazole intravenous solution.

FIG. 8 displays a summary of observed posaconazole steady-state exposures and the projected exposure distribution for the posaconazole intravenous solution. Each box represents 25th to 75th percentiles, the line inside the box represents median value, whiskers represent 10th and 90th percentile, and points beyond whiskers represent outlier values; outliers not shown for projected exposure distribution.

Thus, in some embodiments of the invention, the composition is one that delivers 200 mg of posaconazole to a patient, wherein administration of such a dose results in a $C_{max}$ of about 1470 ng/ml and an $AUC_{last}$ of about 27,000 hr*ng/ml.

Bioequivalent doses and formulations are within the scope of the invention. For systemically absorbed drugs, bioavailability is commonly defined as displaying relevant pharmacokinetic parameters (e.g., $C_{max}$ and AUC) of between 80% and 125% of the reference drug. Thus, in some embodiments of the invention, the composition is one that delivers 200 mg of posaconazole to a patient, wherein administration of such a dose results in a $C_{max}$ of between about 1176 and about 18375 ng/ml, and an $AUC_{last}$ of between about 21,600 and about 33,750 hr*ng/ml.

Methods of Treatment
Anti-Infective Applications

The present invention encompasses methods of prevention and treatment of a variety of infection caused by a broad spectrum of infectious agents. The term "infection" is understood to include, but not be limited to, those disease state caused by molds, yeasts, and other infectious agents such as: *Candida*, dermatophytes, Dimorphics, Dematiaceous, (e.g., *Alternaria* and *Bipoiaris*), *Aspergillus, Acremonium, Basidiomycetes, Bjerkandera, Coprinus, Paecilomyces, Microsporum, Trichophyton, Pseudallescheria, Schizophyllum, Crytococcus, Histoplasma, Blastomyces, Coccidioides, Fusarium, Exophiala, Zygomycocetes* (e.g., *Absidia, Mucor, Rhizopus*, and *Rhizomucor*), *Kluyveromyces, Saccharomyces, Yarrowia, Pichia, Epidermophyton, Paracoccidioides, Scedosporium, Apophysomyces, Curvularia, Penicillium, Fonsecaea, Wangiella, Sporothrix, Pneumocystis, Trichosporon, Cladophialophora, Ramichloridium, Syncephalastrum, Madurella, Scytalidium*, or protozoa such as *Leshmania, Trichomononas* and *Trypanosoma*.

The present invention is intended to treat both opportunistic and non-opportunistic infections, where the term "opportunistic" as used herein denotes those infections caused by organisms capable of causing a disease only in a host whose resistance is lowered, e.g., by chemotherapy or HIV. Posaconazole can be used to treat the progression of invasive fungal infections including prophylaxis, empiric, pre-emptive, primary, and refractory treatments.

In particular, posaconazole is useful in the prevention and/or treatment of the following disease states: Initial (first line) treatment of oropharyngeal or esophageal candidiasis; Salvage therapy of azole-refractory oropharyngeal and esophageal candidiasis (e.g. in patients who have failed oral fluconazole and/or intraconazole); Initial treatment of invasive aspergillosis, candidiasis, fusariosis, scedosporiosis, infections due to dimorphic fungi (e.g., cryptococcosis, *coccidioidomycosis, paracoccidioidomycosis, histoplasmosis, blastomycosis*), zygomycosis, and invasive infections due to rare molds and yeasts; Salvage therapy for invasive mycoses in patients who are refractory to or intolerant of other therapies (e.g., amphotericin B, lipid formulations of amphotericin B, fluconazole, caspofungin, micafungin, anidulafungin, voriconazole and/or intraconazole); Prevention of invasive Candidiasis, invasive mold infections (including *zygomycosis* and *aspergillosis*) in patients at high risk, including patients who have undergone intensive chemotherapy and/or radiation therapy for hematologic malignancies, bone marrow or peripheral stem cell transplant conditioning regimens, and patients receiving combination immunosuppressive therapy for the treatment of acute or chronic graft-versus-host disease or prevention of solid organ transplantation; Chagas disease (*Trypanosomiasis* due to *T. cruzi*) including acute and chronic forms; and Leishmaniasis, including visceral and localized forms.

In some embodiments, the invention encompasses a method of treating or preventing an infection in an animal in need thereof which comprises administering to said animal an effective amount of the formulation. In some embodiments, the animal is a mammal, a bird, a fish, or a reptile.

In some embodiments, the animal is a mammal, including, but not limited to a human.

In some embodiments, the infection is caused by a fungus or parasite.

In some embodiments, the invention encompasses a method wherein said formulation is administered intravenously.

Administration

Immuno-suppressant therapy (e.g. chemotherapy, radiation therapy, myeloablative conditioning regimens) often results in one of more of the above-referenced infections. The present invention encompasses the administration of a posaconazole formulation adjunctive to immuno-suppressant therapy, wherein the posaconazole formulation functions prophylactically with regard to opportunistic infections including the above-referenced disease states.

The present invention encompasses a variety of modes of administration to any part, organ, interstice of cavity of an animal's body that is subject to and infection. A non-limiting set of examples of modes by which the posaconazole formulations of the present invention may be administered includes: intravenously, intramuscularly, via inhalation, or intravascularly.

Co-formulation or co-administrations comprising combinations of posaconazole and at least one other active ingredient are also within the scope of the present invention. Non-limiting examples of such active ingredients include: antifungals such as echinocandins (including caspofungin, micafungin, and anidulafungin) and azoles; amphotericin B; deoxycholate amphotericin B; flucytosine; and terbinafine.

Also within the scope of this invention are combinations with an antibacterial, antiviral, steroid, or nonsteroidal anti-inflammatory drugs ("NSAIDS"), chemotherapeutics, and/or anti-emitics. Similarly, co-administration of Posaconazole with at least one of the above active ingredients, aside from within a single formulation, is also within the scope of the present invention.

In certain embodiments, the pharmaceutical compositions described herein may be administered to a patient in need thereof at a dose of 100 mg to 400 mg every 12 to 24 hours. In certain such embodiments, a dose may comprise at least one intravenous dosage form.

In certain embodiments, the pharmaceutical compositions described herein may be administered to a patient in need thereof at a dose of 100 mg to 400 mg every 12 to 24 hours. In some preferred embodiments, the composition is administered in an amount sufficient to deliver a dose of between about 180 and about 220 mg posaconazole to the patient. In some more preferred embodiments, this dose is about 200 mg posaconazole. The administration may occur once per day or twice per day.

The pharmaceutical compositions of the present invention are administered to a patient according to a dosing regimen. It should be understood that the specific dosing regimen for any particular patient will depend on a variety of factors, including species, age, body weight, body surface area, height, general health, sex, diet, time of administration, rate of excretion, drug combination, specific disease being treated, the severity of the condition, the renal and hepatic function of the patient, the particular active ingredient employed, and the judgment of the treating physician.

Other features and embodiments of the invention will become apparent by the following examples which are given for illustration of the invention rather than limiting its intended scope.

DEFINITIONS

Unless defined otherwise, all technical and scientific terms used herein have the same meaning as those commonly understood by one of ordinary skill in the art to which this invention belongs. Although methods and materials similar or equivalent to those described herein can be used tin the practice or testing of the present invention, suitable methods and materials are described below. The materials, methods and examples are illustrative only, and are not intended to be limiting. All publications, patents and other documents mentioned herein are incorporated by reference in their entirety.

As used herein, the phrase "small-volume parenteral unit" refers to a single-dose or multiple-dose small-volume injection labeled as, or actually containing 100 mL or less.

As used herein, the term "injectable" means adapted to parenteral administration.

As used herein, the term "fungus" includes but is not limited to one of the diverse morphologic forms of yeasts and molds. Fungi include organisms in the following groups or genera: *Candida, dermatophytes, Dimorphics, Dematiaceous,* (e.g., *Alternaria* and Bipolar's), *Aspergillus, Acremonium, Basidiomycetes, Bjerkandera, Coprinus, Paecilomyces, Microsporum, Trichophyton, Pseudallescheria, Schizophyllum, Crytococcus, Histoplasma, Blastomyces, Coccidioides, Fusarium, Exophiala, Zygomycocetes* (e.g., *Absidia, Mucor, Rhizopus,* and *Rhizomucor*), *Kluyveromyces, Saccharomyces, Yarrowia, Pichia, Epidermophyton, Paracoccidioides, Scedosporium, Apophysomyces, Curvularia, Penicillium, Fonsecaea, Wangiella, Sporothrix, Pneumocystis, Trichosporon, Cladophialophora, Ramichloridium, Syncephalastrum, Madurella, Scytalidium,* or protozoa such as *Leshmania, Trichomononas* and *Trypanosome*.

As used herein, the term "Dematiaceous" means dark-walled conidia and/or hyphae, and includes as non-limiting examples: *Alternaria,* and *Bipolaris*. Phaeohyphomycosis is an example of a Dematiaceous fungal infection.

As used herein, the term "parasite" means an organism that lives on or in another and draws its nourishment from them. Parasites include *Leishmania, Trypanosoma,* and *Trichomonas*, among others.

As used herein, the term "AUC" is the area under the plasma concentration-time curve from time zero to a certain time period of the sample. For example, AUC (4 h) means the area under the plasma concentration-time curve from time zero to 4 hours.

The term "patient" refers to an animal including a mammal (e.g. human).

The term "pharmaceutically acceptable excipient" refers to a non-toxic excipient that may be administered to a patient, together with the weakly basic and poorly-aqueous soluble azoles as describe herein, which does not destroy the pharmacological activity thereof.

The term "treating" or "treatment" is intended to mean prophylactic use to prevent disease or mitigating or alleviating the symptoms of the recited condition, disease or disorder in a mammal such as a human.

The term "pharmacokinetics" refers to the process by which a drug is absorbed, distributed, metabolized and eliminated by the body. Pharmacokinetic parameters include, but are not limited to "maximum plasma concentration" or "$C_{max}$", "area under the plasma concentration time curve or "AUC", and "time to $C_{max}$" or "$T_{max}$".

As used herein, the term "$t_{1/2}$" refers to the half-life of the drug.

The present invention is not to be limited in scope by the specific embodiments describe herein. Indeed, various modification of the invention in addition to those described herein will become apparent to those skilled in the art from the foregoing description. Such modifications are intended to fall within the scope of the appended claims.

What is claimed:

1. A pharmaceutical composition for intravenous administration comprising:

posaconazole, or a pharmaceutically acceptable salt thereof; and a modified β-cyclodextrin which comprises sulfobutylether-β-cyclodextrin having a degree of substitution of 6.5 and a molecular weight of 2163 g/mole;

in aqueous solution, wherein the pH of said composition is between about 2.0 and about 3.5, wherein the concentration of said posaconazole, or pharmaceutically acceptable salt thereof, is between about 14 and about 22 mg/mL, and the concentration of said modified β-cyclodextrin is between about 350 and about 450 mg/mL.

2. The composition according to claim 1, further comprising a chelating agent.

3. The composition according to claim 2, wherein said pharmaceutical composition comprises posaconazole free base, said chelating agent comprises EDTA, and wherein said pH is between about 2.3 and about 3.0.

4. The composition according to claim 3, wherein the concentration of said EDTA is between about 0.1 and about 0.3 mg/mL.

5. The composition according to claim 3, wherein the concentration of said posaconazole free base is about 18 mg/mL, the concentration of said sulfobutylether-β-cyclodextrin is about 400 mg/mL, and the concentration of said EDTA is about 0.2 mg/mL.

6. The composition according to claim 1, wherein administration of a dose of said composition that delivers 200 mg of posaconazole to a patient results in a $C_{max}$ of between about 1176 and about 18375 ng/ml, and an $AUC_{last}$ of between about 21,600 and about 33,750 hr*ng/ml.

7. The composition according to claim 1, wherein administration of a dose of said composition that delivers 200 mg of posaconazole to a patient results in a $C_{max}$ of about 1470 ng/ml and an $AUC_{last}$ of about 27,000 hr*ng/ml.

8. A pharmaceutical composition comprising components and the quantities of each as follows:

| Components | Quantity |
| --- | --- |
| Posaconazole | about 18 mg/mL |
| sulfobutylether-β-cyclodextrin sodium salt, molecular weight 2163 g/mole (degree of substitution = 6.5), solubility > 800 mg/mL in water | about 400 mg/mL (185 mM) |
| Disodium Edetate (EDTA) | about 0.2 mg/mL |
| 1N Hydrochloric Acid | sufficient quantity to adjust to pH of about 2.6 |
| 1N Sodium Hydroxide | sufficient quantity to adjust to pH of about 2.6 |
| Water | q.s. ad 1 mL. |

9. A method of treating an infection in an animal in need thereof which comprises administering to said animal an effective amount of the pharmaceutical composition of claim 1.

10. The method of claim 9 where said infection is caused by a fungus or a parasite.

11. The method of claim 9 wherein said infection is one or more selected from the group consisting of: oropharyngeal or esophageal candidiasis;

refractory oropharyngeal and esophageal candidiasis; invasive aspergillosis, candidiasis, fusarriosis, scedosporiosis, infections due to dimorphic fungi, zygomycosis, and invasive infections due to rare molds and yeasts; invasive mycoses in patients who are refractory to, or intolerant of, other therapies; Candidiasis, invasive mold infections in patients who have undergone intensive chemotherapy and/or radiation therapy for hematologic malignancies, bone marrow or peripheral stem cell transplant conditioning regimes, and patients receiving combination immunosuppressive therapy for the treatment of acute or chronic graft-versus-host disease; Chagas disease; and Leishmaniasis.

12. A pharmaceutical composition according to claim 1, wherein after said composition has been injected into an infusion bag, the composition and the infusate have been admixed, and the resulting admixture has been allowed to stand for up to 24 hours, no posaconazole precipitate is visible.

13. A method of treating an infection in an animal in need thereof which comprises administering to said animal the composition of claim 1 in an amount sufficient to deliver a dose of between about 180 and about 220 mg posaconazole to said animal.

14. A method of treating an infection in an animal in need thereof which comprises administering to said animal the composition of claim 1 in an amount sufficient to deliver a dose of about 200 mg posaconazole to said animal.

15. The method according to claim 13 wherein said administration occurs once per day.

16. The method according to claim 13 wherein said administration occurs twice per day.

17. The method of claim 9 further comprising administering a second active ingredient selected from one or more of the group consisting of antifungals, antibacterials, antivirals, steroids, nonsteroidal anti-inflammatory drugs, chemotherapeutics and anti-emetics.

18. The method of claim 9 wherein said antifungals are selected from the group consisting of azoles, echinocandin, allylamine, polyene, flucytosine, benzoic acid, ciclopirox, 1,3-dihydro-5-fluoro-1-hydroxy-2,1-benzoxaborate, tolnaftate, undecyclenic acid, griseofulvin and haloprogin.

19. A kit comprising:
a small, breakable container;
an infusion bag;
and the composition of claim 1,
wherein said container contains the composition of claim 1,
and said infusion bag contains a diluent selected from the group consisting of normal saline solution and 5% dextrose solution,
and wherein said small, breakable container is placed directly inside said infusion bag suitably to allow said composition to be diluted by breaking said small, breakable container directly inside diluent in said infusion bag.

* * * * *